United States Patent
Maltz et al.

(10) Patent No.: US 10,255,484 B2
(45) Date of Patent: Apr. 9, 2019

(54) METHOD AND SYSTEM FOR ASSESSING FACIAL SKIN HEALTH FROM A MOBILE SELFIE IMAGE

(71) Applicant: Xerox Corporation, Norwalk, CT (US)

(72) Inventors: Martin S. Maltz, Rochester, NY (US); Matthew Adam Shreve, Webster, NY (US); Luisa Fernanda Polania Cabrera, Webster, NY (US); Stephen C. Morgana, Rochester, NY (US); Raja Bala, Pittsford, NY (US); Paul Jonathan Matts, Surrey (GB); Ankur Purwar, Sunglade (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/414,095

(22) Filed: Jan. 24, 2017

(65) Prior Publication Data
US 2017/0270350 A1    Sep. 21, 2017

Related U.S. Application Data

(60) Provisional application No. 62/311,192, filed on Mar. 21, 2016.

(51) Int. Cl.
| | |
|---|---|
| *G06K 9/00* | (2006.01) |
| *G09B 19/00* | (2006.01) |
| *A61B 5/00* | (2006.01) |
| *G06Q 30/06* | (2012.01) |
| *G06T 7/40* | (2017.01) |

(Continued)

(52) U.S. Cl.
CPC ........ *G06K 9/00281* (2013.01); *A61B 5/0022* (2013.01); *A61B 5/0077* (2013.01); *A61B 5/443* (2013.01); *A61B 5/486* (2013.01); *A61B 5/742* (2013.01); *G06Q 30/0631* (2013.01); *G06T 7/40* (2013.01); *G06T 7/90* (2017.01); *G09B 19/00* (2013.01); *G06K 2009/4666* (2013.01);

(Continued)

(58) Field of Classification Search
None
See application file for complete search history.

(56) References Cited

U.S. PATENT DOCUMENTS

| | | |
|---|---|---|
| 5,983,120 A | 11/1999 | Groner et al. |
| 8,077,931 B1 | 12/2011 | Chatman |

(Continued)

OTHER PUBLICATIONS

All Office Actions, U.S. Appl. No. 15/414,002.

(Continued)

*Primary Examiner* — Kevin Ky
(74) *Attorney, Agent, or Firm* — John G. Powell (57) ABSTRACT

A method, non-transitory computer readable medium and apparatus for transmitting an assessment of facial skin health of a customer are disclosed. For example, the method includes receiving an image of a customer from a mobile endpoint device of the customer, analyzing one or more parameters of a facial skin of the customer in the image of the customer, determining the assessment of facial skin health of the customer based on the one or more parameters of the facial skin that are analyzed and transmitting the assessment of facial skin health to the mobile endpoint device of the customer to cause the mobile endpoint device to automatically display the assessment of facial skin health.

17 Claims, 7 Drawing Sheets

(51) Int. Cl.
*G06T 7/90* (2017.01)
*H04N 1/00* (2006.01)
*G06K 9/46* (2006.01)

(52) U.S. Cl.
CPC ............ *G06T 2207/10024* (2013.01); *G06T 2207/30201* (2013.01); *H04N 1/00106* (2013.01)

(56) References Cited

U.S. PATENT DOCUMENTS

| | | | |
|---|---|---|---|
| 2007/0071314 A1* | 3/2007 | Bhatti | G06K 9/6212 382/162 |
| 2007/0104472 A1 | 5/2007 | Quan | |
| 2008/0080746 A1* | 4/2008 | Payonk | G06K 9/00281 382/118 |
| 2008/0194928 A1* | 8/2008 | Bandic | G16H 15/00 600/306 |
| 2009/0245603 A1* | 10/2009 | Koruga | A45D 44/00 382/128 |
| 2010/0172567 A1* | 7/2010 | Prokoski | A61B 5/0064 382/132 |
| 2011/0016001 A1 | 1/2011 | Schieffelin | |
| 2011/0196616 A1 | 8/2011 | Gunn | |
| 2012/0223131 A1 | 9/2012 | Lim | |
| 2013/0041733 A1 | 2/2013 | Officer | |
| 2013/0079620 A1* | 3/2013 | Kuth | G06T 7/0012 600/407 |
| 2013/0094780 A1* | 4/2013 | Tang | G06T 11/60 382/284 |
| 2013/0158968 A1* | 6/2013 | Ash | G16H 40/63 703/11 |
| 2014/0089017 A1 | 3/2014 | Klappert et al. | |
| 2014/0201126 A1 | 7/2014 | Zadeh | |
| 2014/0209682 A1 | 7/2014 | Gottwals et al. | |
| 2014/0211022 A1 | 7/2014 | Koh et al. | |
| 2014/0219526 A1* | 8/2014 | Linguraru | G06K 9/00281 382/128 |
| 2014/0270490 A1* | 9/2014 | Wus | G06K 9/00234 382/159 |
| 2014/0334723 A1 | 11/2014 | Chatow | |
| 2015/0045631 A1 | 2/2015 | Penderson | |
| 2016/0162728 A1 | 6/2016 | Arai et al. | |
| 2017/0246473 A1* | 8/2017 | Marinkovich | A61N 5/0616 |
| 2017/0270348 A1 | 9/2017 | Morgana et al. | |
| 2017/0270349 A1 | 9/2017 | Polania Cabrera et al. | |
| 2017/0270691 A1 | 9/2017 | Maltz et al. | |
| 2017/0272741 A1 | 9/2017 | Maltz et al. | |

OTHER PUBLICATIONS

All Office Actions, U.S. Appl. No. 15/414,147.
All Office Actions, U.S. Appl. No. 15/414,189.
All Office Actions, U.S. Appl. No. 15/414,305.
Finlayson et al., Color by Correlation: A Simple, Unifying Framework for Color Constancy, IEEE Transactions on Pattern Analysis and Machine Intelligence, vol. 23, No. 11, Nov. 2001, pp. 1209-1221.
Gong et al., Quantification of Pigmentation in Human Skin Images, IEEE, 2012, pp. 2853-2856 no date available.
Hyvarinen et al., A Fast Fixed-Point Algorithm for Independent Component Analysis of Complex Valued Signals, Neural Networks Research Centre, Helsinki University of Technology, Jan. 2000, 15 pages.
Hyvarinen et al., A Fast Fixed-Point Algorithm for Independent Component Analysis, Neural Computation, 9:1483-1492, 1997 no date available.
Ojima et al., Application of Image-Based Skin Chromophore Analysis to Cosmetics, Journal of Imaging Science and Technology, vol. 48, No. 3, May 2004, pp. 222-226.
Sun et al., Statistical Characterization of Face Spectral Reflectances and Its Application to Human Portraiture Spectra Estimation, Journal of Imaging Science and Technology, vol. 46, No. 6, 2002, pp. 498-506 no date available.
Tsumura et al., Image-based skin color and texture analysis/synthesis by extracting hemoglobin and melanin information in the skin, ACM Transactions on Graphics (TOG), vol. 22, Issue 3, Jul. 2003, pp. 770-779.

* cited by examiner

METHOD AND SYSTEM FOR ASSESSING FACIAL SKIN HEALTH FROM A MOBILE SELFIE IMAGE

CROSS REFERENCE TO RELATED APPLICATIONS

This application claims priority under 35 U.S.C. § 119(e) to U.S. provisional patent application Ser. No. 62/311,192, filed on Mar. 21, 2016, which is hereby incorporated by reference in its entirety.

The present disclosure relates generally to facial image analysis and, more particularly, to a method and system for assessing facial skin health from a mobile selfie image.

BACKGROUND

Some companies are beginning to develop products or applications to improve a consumer's skincare experience. The applications look to provide product recommendations and navigation solutions. The applications can also provide personalized skincare for the customer by providing continuous support, educating the user about skin biology, tracking the customer's skin performance over time, and customizing product and regiment solutions to the customer's individual needs.

One challenge to providing such applications is an ability to receive an accurate image of the customer's face and providing an accurate analysis of the customer's face based on the image. Some solutions may require the customer to come to a lab or a studio of the company to take images with high quality cameras in a controlled light setting. However, requiring the customer to travel to another lab or studio is time consuming and inconvenient to the customer.

Another option may be to analyze images provided by the customer. However, images provided by the customer can have a large amount of variation in image quality and lighting.

SUMMARY

According to aspects illustrated herein, there are provided a method, non-transitory computer readable medium and system for transmitting an assessment of facial skin health of a customer. One disclosed feature of the embodiments is a method that receives an image of a customer from a mobile endpoint device of the customer, analyzes one or more parameters of a facial skin of the customer in the image of the customer, determines the assessment of facial skin health of the customer based on the one or more parameters of the facial skin that are analyzed and transmits the assessment of facial skin health to the mobile endpoint device of the customer to cause the mobile endpoint device to automatically display the assessment of facial skin health.

Another disclosed feature of the embodiments is a non-transitory computer-readable medium having stored thereon a plurality of instructions, the plurality of instructions including instructions which, when executed by a processor, cause the processor to perform operations that receive an image of a customer from a mobile endpoint device of the customer, analyze one or more parameters of a facial skin of the customer in the image of the customer, determine the assessment of facial skin health of the customer based on the one or more parameters of the facial skin that are analyzed and transmit the assessment of facial skin health to the mobile endpoint device of the customer to cause the mobile endpoint device to automatically display the assessment of facial skin health.

Another disclosed feature of the embodiments is an apparatus comprising a processor and a computer-readable medium storing a plurality of instructions which, when executed by the processor, cause the processor to perform operations that receive an image of a customer from a mobile endpoint device of the customer, analyze one or more parameters of a facial skin of the customer in the image of the customer, determine the assessment of facial skin health of the customer based on the one or more parameters of the facial skin that are analyzed and transmit the assessment of facial skin health to the mobile endpoint device of the customer to cause the mobile endpoint device to automatically display the assessment of facial skin health.

BRIEF DESCRIPTION OF THE DRAWINGS

The teaching of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

The present disclosure broadly discloses a method and system for assessing facial skin health from a mobile selfie image. As discussed above, some companies are beginning to develop products or applications to improve a consumer's skincare experience. In doing so, an image of the customer can be used to analyze the health of the customer's skin. The image of the customer's skin can be analyzed and feedback of the analysis can be provided back to the user as an assessment of facial skin health.

Embodiments of the present disclosure provide a system that can capture mobile selfie images, transmit the mobile selfie image for analysis of the facial skin of the customer, and then transmit an assessment of facial skin health of a customer based on the analysis. The assessment of facial skin health may be provided as a general binary outcome (e.g., good or bad), as a score, as a visual map, or any combination thereof.

Figure 1:
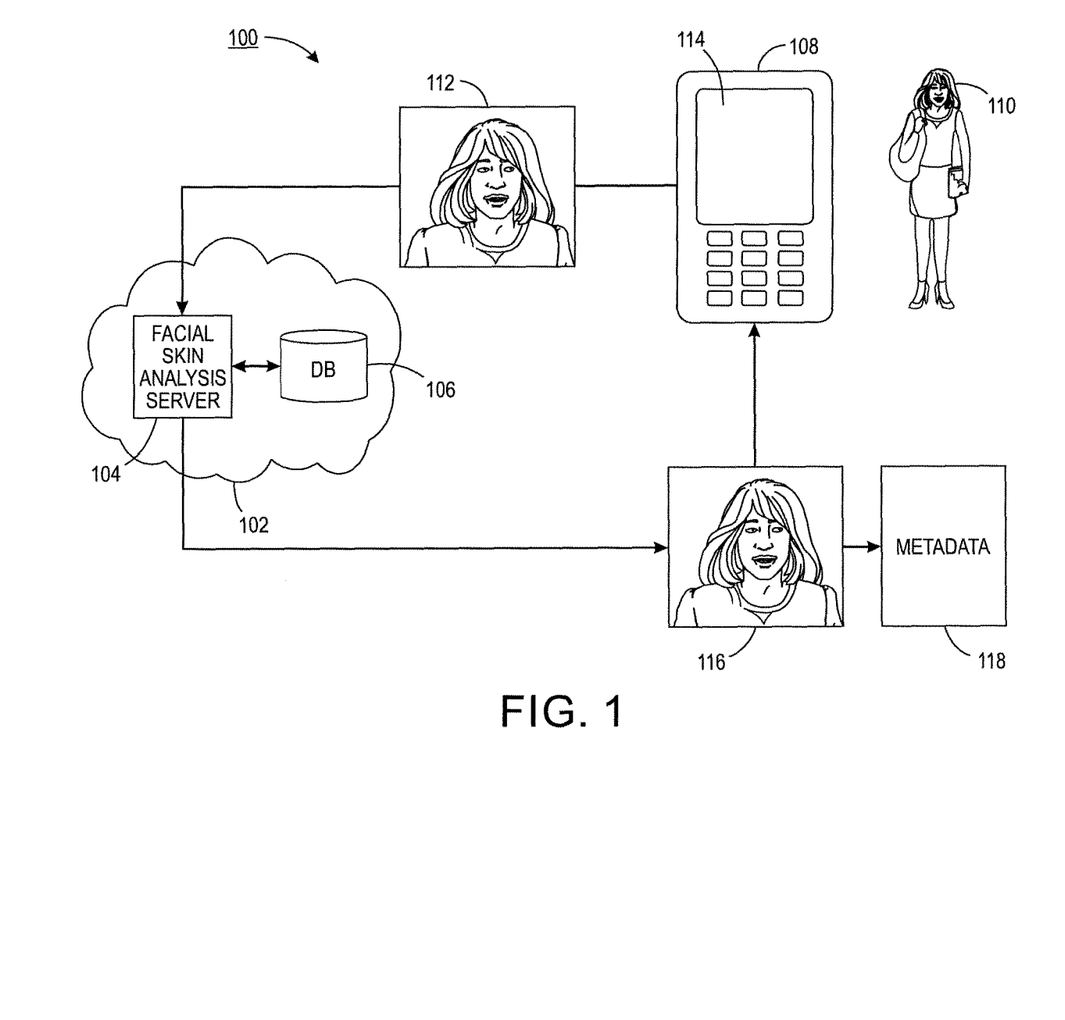
FIG. 1 illustrates an example block diagram of a communication network of the present disclosure.

FIG. 1 illustrates an example system 100 of the present disclosure. In one embodiment, the system 100 may include a communication network 102. The communication network 102 may be any type of wired or wireless communication network. In one embodiment, the communication network 102 may be an Internet Protocol (IP) network.

It should be noted that the communication network 102 has been simplified for ease of explanation. For example, the communication network 102 may include one or more additional network elements (e.g., a router, a gateway, a border element, switches, and the like) or access networks (e.g., a cellular access network, a broadband access network, and the like) that are not shown.

In one embodiment, the communication network 102 may include a facial skin analysis server (FSAS) 104 and a database (DB) 106. In one embodiment, the FSAS 104 may establish a wired or wireless connection with one or more mobile endpoint devices 108 to receive and transmit images to the one or more mobile endpoint devices 108 and perform the functions described herein.

In one embodiment, the DB 106 may store various information associated with the functions described herein. For example, the DB 106 may store graphs generated based on training images, one or more images 112 received from the one or more endpoint devices 108 of one or more customers 110 (also referred to herein generically as "a user" or "users"), generated graphical chromophore maps, an assessment of facial skin health 116 generated by the FSAS 104, metadata 118, and the like.

It should be noted that although FIG. 1 illustrates a single mobile endpoint device 108, a single customer 110, a single FSAS 104, and a single DB 106, that any number of mobile endpoint devices, customers, FSASs and DBs may be deployed. For example, multiple FSAS 104 may be deployed to perform a distributed processing of the images 112. In another example, a plurality of mobile endpoint devices 108 may be sending images of different customers 110 to be analyzed and processed to calculate an assessment of facial skin health 116 for each customer 110.

Figure 2:
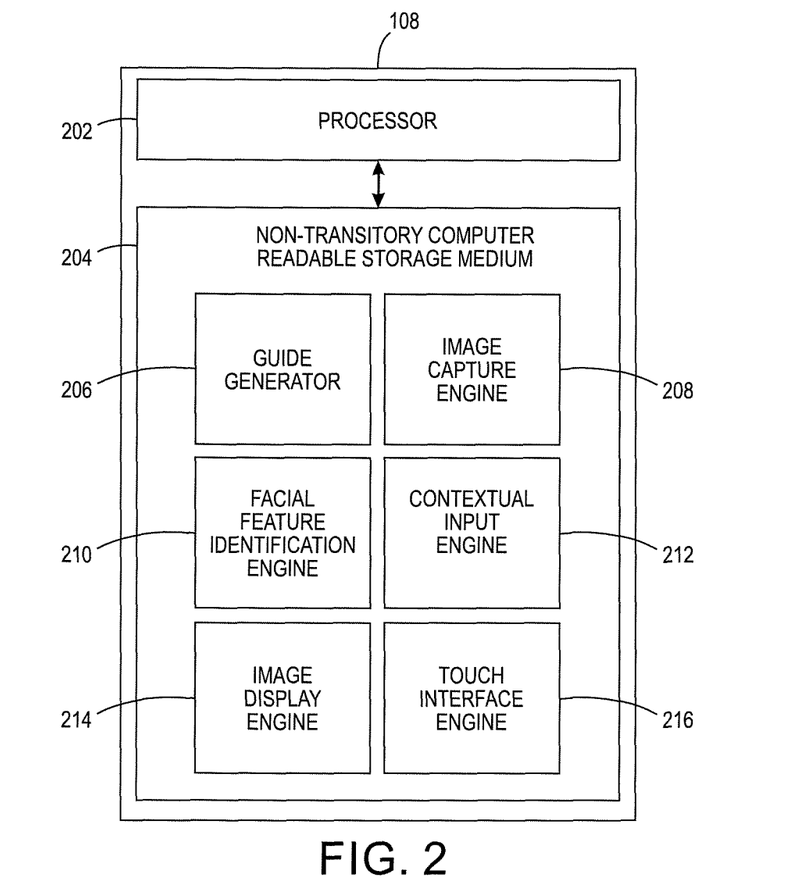
FIG. 2 illustrates an example apparatus of the present disclosure.

In one embodiment, the mobile endpoint device 108 may include a mobile skin care application. The mobile skin care application may be used to help provide a customized skincare experience for the customer 110. FIG. 2 illustrates one example of the mobile endpoint device 108.

In one embodiment, the mobile endpoint device 108 may include a processor 202 and a non-transitory computer readable storage medium 204. In one embodiment, the non-transitory computer readable storage medium 204 may include engines or modules that include instructions that are executed by the processor 202 to perform the functions described herein. For example, the non-transitory computer readable storage medium 204 may include the mobile skin care application that is executed by the processor 202.

In one embodiment, the non-transitory computer readable storage medium 204 may include a guide generator 206, an image capture engine 208, a facial feature identification engine 210, a contextual input engine 212, an image display engine 214 and a touch interface engine 216. In one embodiment, the guide generator 206 may generate and display a guide 404 illustrated in FIG. 4.

Figure 4:
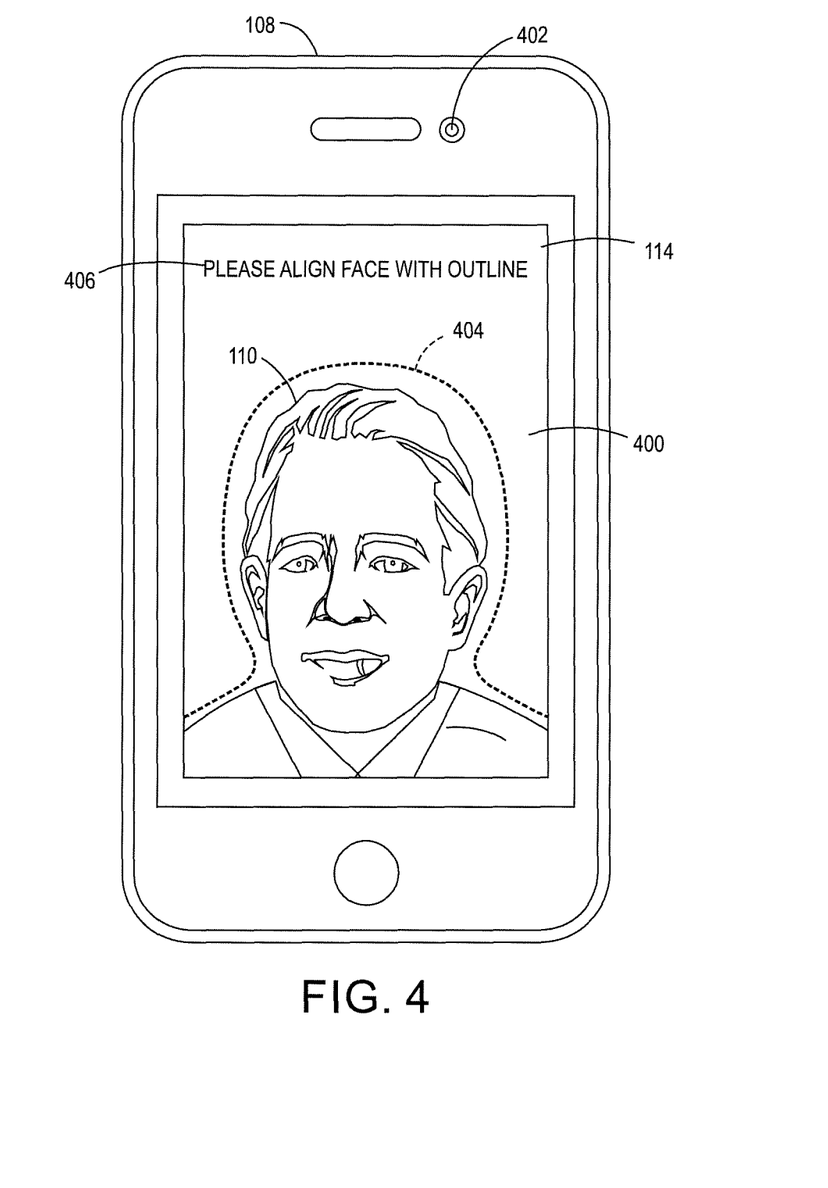
FIG. 4 illustrates an example graphical user interface of the present disclosure.

For example, the mobile skin care application may leverage a camera 402 and/or a flash (not shown) of the mobile endpoint device 108 to capture the image 112 of the customer 110. The image 112 may also be referred to as a mobile selfie image. In other words, the image 112 captures a face or headshot of the customer 110.

In one embodiment, a display 114 of the mobile endpoint device may help position the face of the customer 110 properly to capture a proper image 112 using the guide 404. For example, the display 114 may display the guide 404 to allow the customer 110 to properly position his or her head, or face, at a proper angle, at a proper size, with a proper amount of lighting, and the like.

FIG. 4 illustrates one example of a graphical user interface (GUI) 400 that illustrates the guide 404. In one embodiment, the camera 402 of the mobile endpoint device 108 may be pointed at the face of the customer 110. The display 114 may display an image of the customer 110. Overlaid on top of the image of the customer 110 may be the guide 404 illustrated by dashed lines.

In one embodiment, the guide 404 may initially have a generic shape of a model head or face at a desired angle (e.g., straight on, turned three-quarters, looking slightly up, and the like). After a first time the image 112 is captured, the guide 404 may be customized to have a shape that corresponds to the shape of the head, or face, of the customer 110. Thus, the guide 404 may be different for each customer after each initial use. As more images 112 of the customer 110 are taken, the guide 404 may gradually be modified to be more accurate.

In one embodiment, the guide 404 may ensure that the face of the customer 110 is at a proper position with respect to an angle or amount of turn and a size. In one embodiment, the display 114 may also include a message 406 to help guide the customer 110. For example, if the customer 110 is not aligned with the guide 404, the message 406 may notify the customer 110 to align his or her face with the outline of the guide 404. In another embodiment, the message 406 may notify the customer 110 if there is not enough light. For example, the message 406 may indicate to turn on the flash of the mobile endpoint device, retake the picture in a brighter room, and the like.

Referring back to FIG. 2, in one embodiment, the image capture engine 208 may then automatically take a plurality of images 112 once the face of the customer 110 is properly positioned. For example, the plurality of images 112 may be taken at different settings. For example, the plurality of images 112 may be taken at different f/stops to vary the exposure of each one of the plurality of images 112 to ensure that the FSAS 104 has a proper image 112 for analyzing.

In one embodiment, the facial feature identification engine 210 may identify a plurality of facial regions of the face of the customer 110 from the image 112. In one embodiment, the plurality of facial regions may be identified using a D-lib based face detector. The D-lib based face detector is an algorithm that provides facial landmark points. For example, a total of 68 landmark points may be detected on the face (e.g., the boundary of the eyes, face, lips, and the like) using D-lib. Since the landmark locations may be fixed (e.g., point 1 is always the upper cheek and point 28 is always the top left of the left eye) polygonal regions may be drawn on the face by drawing lines between certain points of the 68 landmark points. For example, the facial regions of the forehead, the left eye and right eye, under the left and right eye, the left cheek, the right cheek and the chin may be drawn. In another example, these points may be inferred based on models of the face to generate curved boundaries of each facial regions. In addition, the models of the face may be trained manually based on statistical ratios of the face, or using an automatic or semi-automatic approach that learns these regions from labeled data.

A mask may be created for each of the shapes defined by the facial regions that are drawn. The masks may consist of the same number of pixels as the original areas in the image 112. In addition, each pixel of the mask may be a binary value that indicates whether the pixel is inside of a respective mask or not (e.g., a value of 1 if the pixel is within a respective mask or a value of 0 if the pixel is outside of the respective mask). A polygon may also be generated for each facial shape region for later operations based on the polygons, such as, detecting user touches within a region on his or her displayed face.

Then, logical operations can be performed on the image 112, thus, restricting analysis to a region of interest. For instance, if a local "AND" operation is done between the mask and image 112, all pixel values at locations outside of the mask may be set to 0, while the pixel values at locations inside of the defined mask region may be unchanged.

A mask can comprise multiple regions by performing logical "OR" operations. For example, if the left cheek mask is OR'ed with the right cheek mask, a new mask may be generated that consists of both cheeks.

In one embodiment, the contextual input engine 212 may receive contextual input from the customer 110. For example, the customer 110 may enter contextual input (e.g., text, a description, a note, a question, and the like) for a particular facial region. For example, the customer 110 may note that a scar is located from a childhood accident in the forehead region, or that the customer 110 suffers from a medical skin condition, such as rosacea, in both cheek regions, ask if a spot on the chin region of the customer 110 is abnormal, and the like. The contextual input may be associated with specific facial regions and added to the image 112 for transmission to the FSAS 104.

In one embodiment, the image display engine 214 may display the image 112 that is captured for review and approval and/or display the assessment of facial skin health 116 and the metadata 118. For example, the image display engine 214 may format the image 112 or the assessment of facial skin health 116 for proper display via the display 114 of the mobile endpoint device 108. For example, the image display engine 214 may ensure that the image 112 or the assessment of facial skin health 116 is displayed with a correct color, at a correct resolution, at a correct aspect ratio, and the like.

In one embodiment, the touch interface engine 216 may detect when the customer 110 has selected a portion of the assessment of facial skin health 116 that is displayed and interpret the selection with respect to the assessment of facial skin health 116. For example, as discussed in further detailed below, after the image 112 is analyzed one or more parameters may be associated with each facial region of the image 112. The assessment of facial skin health 116 may be calculated based on the image 112 and the one or more parameters associated with each facial region.

Figure 5:
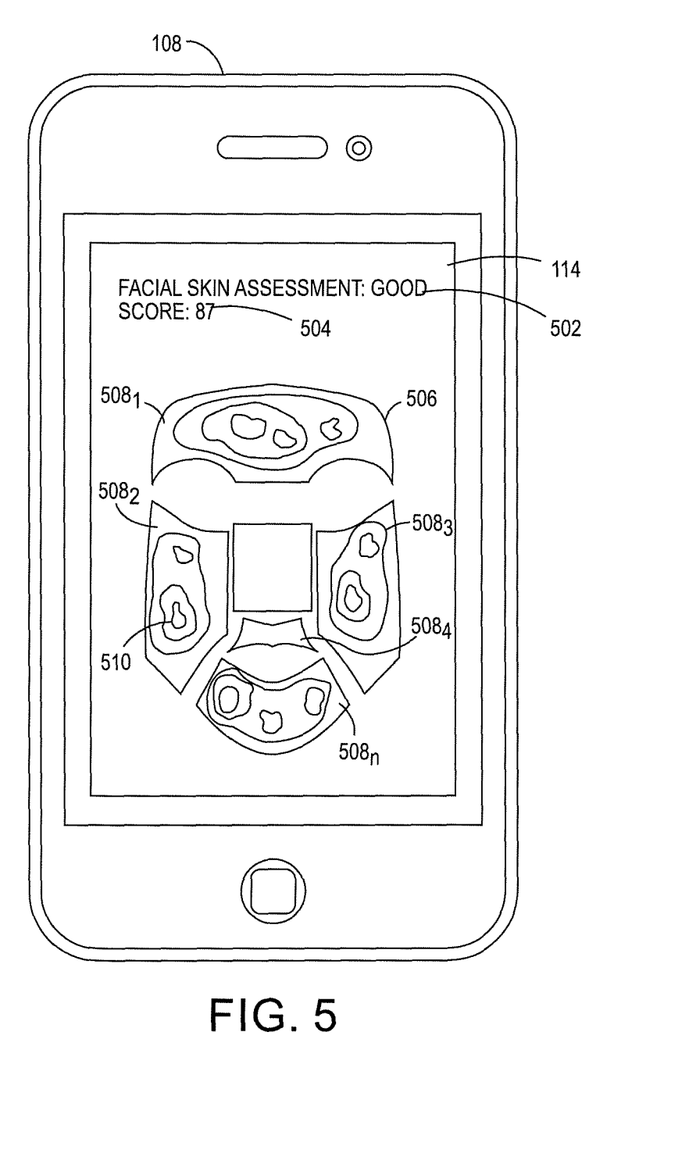
FIG. 5 illustrates an example assessment of facial skin health.

The assessment of facial skin health 116 may be displayed to the customer 110. FIG. 5 illustrates an example of the assessment of facial skin health 116 that is displayed to the customer 110. In one embodiment, assessment of facial skin health 116 can be displayed on the display 114 of the mobile endpoint device 108.

In one embodiment, the assessment of facial skin health 116 may display a binary outcome 502 based on the one or more parameters that are analyzed, as discussed below. For example, the binary outcome 502 may indicate that the assessment of facial skin health is either good or bad.

In one embodiment, the assessment of facial skin health 116 may display a numerical score 504. In one embodiment, the numerical score may be based upon a weighted score of each one of the one or more parameters that are analyzed, as discussed below. The numerical score may indicate a range of assessments of facial skin health. For example, 60 and below may be bad, 61-70 may be needs improvement, 71-80 may be average, 81-90 may be good and 91-100 may be excellent. It should be noted that the gradation and numerical values are provided as examples. The numerical score range can be any range of values. In one embodiment, a letter grade (e.g., A, B, C, D and F) may be provided instead of a numerical value.

In one embodiment, the assessment of facial skin health 116 may display a visual map 506. The visual map 506 may be divided into facial regions $508_1$ to $508_n$ (also referred to herein individually as facial region 508 or collectively as facial regions 508). Within each facial region 508 a localized assessment of facial skin health 116 may be displayed as shown by concentric areas 510. For example, each area 510 may have a different color (e.g., similar to a heat map). For example, areas 510 of bad health may have a red color that gradually change shades of color to areas 510 of good health that may have a blue color (e.g., gradual change from red, to light red, to orange, to yellow, to light blue to blue). It should be noted that the color scheme is provided only as an example and that any combination of colors or gradual changing color scheme can be used. In one embodiment, different shapes or different shadings may be deployed instead of different colors.

In one embodiment, the customer 110 may select a facial region 508 to zoom in on the selected facial region 508. The facial region 508 that is selected may be enlarged and a more detailed view of the visual map may be illustrated. For example, the areas 510 may have a more defined contour, outline, gradation, and the like.

In one embodiment, the assessment of facial skin health 116 may be displayed as different graphical chromophore maps based on different chromophore components that are separated (e.g., a melanin graphical chromophore map or a hemoglobin graphical chromophore map). In one embodiment, the assessment of facial skin health 116 may be displayed as illustrating lines where wrinkles, pores, acne, moles, and the like, are identified overlaid on the image 112. For example, the assessment of facial skin health 116 may have a menu to allow the customer 110 to view any image or visualization of the assessment of facial skin health 116 described above.

Figure 3:
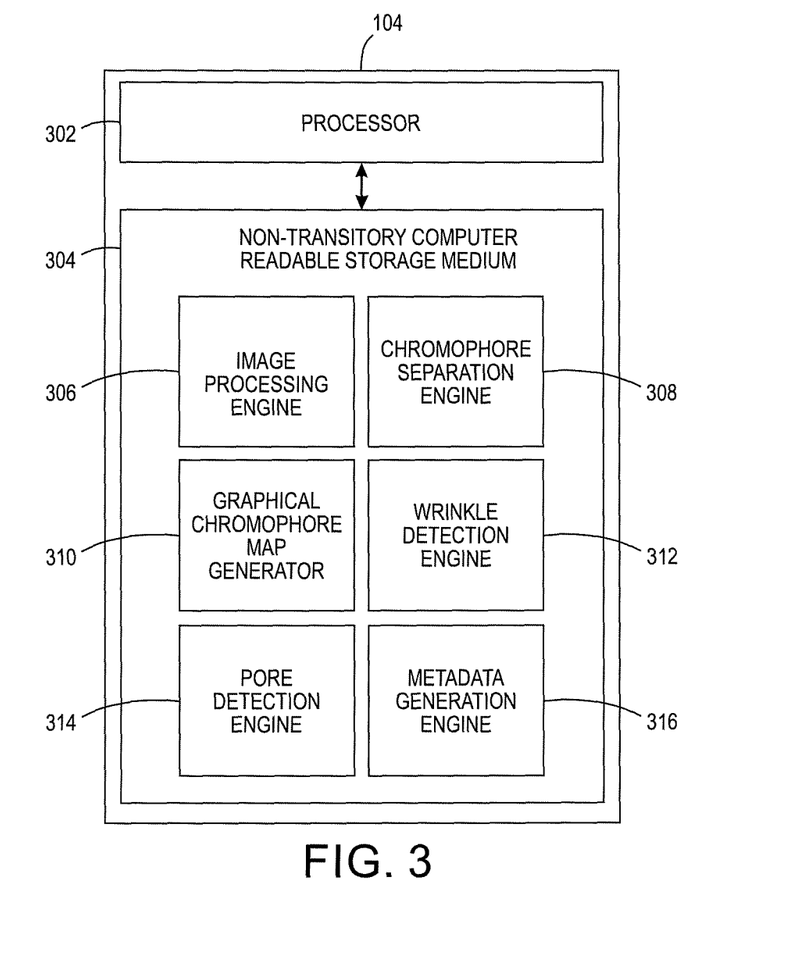
FIG. 3 illustrates an example facial skin analysis server of the present disclosure.

Referring back to FIG. 1, the mobile endpoint device 108 may send the image 112 to the FSAS 104 for processing to generate the assessment of facial skin health 116 and the metadata 118. FIG. 3 illustrates an example of the FSAS 104.

In one embodiment, the FSAS 104 may include a processor 302 and a non-transitory computer readable storage medium 304. In one embodiment, the non-transitory computer readable storage medium 304 may include engines or modules that include instructions that are executed by the processor 302 to perform the functions described herein. For example, the non-transitory computer readable storage medium 304 may include the mobile skin care application that is executed by the processor 302.

In one embodiment, the non-transitory computer readable storage medium 304 may include an image processing engine 306, a chromophore separation engine 308, a graphical chromophore map generator 310, a wrinkle detection engine 312, a pore detection engine 314, and a metadata generation engine 316. In one embodiment, the image processing engine 306 may be used to receive the image 112 that is taken in the red, green, blue (RGB) color space and convert the image 112 into a spectral representation. The spectral representation may then be used to perform chromophore separation that is used to determine an amount of melanin and hemoglobin in areas of the facial skin and to generate the graphical chromophore maps, as described by co-pending U.S. Patent Provisional Application Ser. No.

62/311,175, entitled "METHOD AND APPARATUS FOR GENERATING GRAPHICAL CHROMOPHORE MAPS," filed on Mar. 21, 2016, which is incorporated by reference in its entirety.

In one embodiment, if the mobile endpoint device 108 is unable to identify a plurality of facial regions, as described above, the image processing engine 306 may identify the plurality of facial regions from the image 112. In other words, either the mobile endpoint device 108 or the FSAS 104 may identify the plurality of facial regions using the techniques described above.

In one embodiment, the image processing engine 306 may also calculate and generate the assessment of facial skin health 116. For example, the assessment of facial skin health may be based on the one or more parameters that are analyzed from the image 112 by the various engines 308, 312, 314 and 316, as described below. In one embodiment, the image processing engine 306 may calculate and display the assessment of facial skin health 116 as a binary outcome based upon a predefined threshold, as illustrated in FIG. 5. For example, the binary outcome may simply be an assessment that the facial skin health of the customer 110 is good or bad. For example, each one of the one or more parameters may be associated with a respective threshold value that determines if a particular parameter is good or bad. If each one of the one or more parameters is below the respective threshold value and are determined to be good, then the assessment of facial skin health 116 may display that facial skin health of the customer 110 is good.

In another embodiment, the predefined threshold value for the assessment of facial skin health 116 may be a percentage of the one or more parameters being above the respective threshold. For example, if 80% or more of the one or more parameters being analyzed are below the respective thresholds, then the assessment of facial skin health 116 may be calculated as being good.

In one embodiment, the assessment of facial skin health 116 may be calculated and displayed as a numerical score, as illustrated in FIG. 5. For example, each one of the one or more parameters may be converted into a numerical score (e.g., on a scale of 1-100, 0-10, and the like). The numerical score for each one of the one or more parameters may be added or averaged for an overall score that may be displayed as the assessment of facial skin health 116.

In one embodiment, the one or more parameters may be weighted. For example, if a facial skin expert determines one parameter is more important than other parameters, the one parameter may have a higher weighting (e.g., the important parameter may be weighted 40% and a remaining three parameters may be each weighted 20%). In another example, the customer 110 may place an importance on a particular parameter (e.g., melanin content may be weighted higher by the customer because good texture is important to the customer 110). Then the parameter selected by the customer 110 may be weighted more heavily in the overall numerical score than other parameters.

In one embodiment, the assessment of facial skin health 116 may be calculated and displayed as a visual map, as illustrated in FIG. 5. For example, each score or binary outcome of each one of the one or more parameters may be color coded. Each facial region may be analyzed on a pixel by pixel basis to determine assessment of facial skin health 116 for a particular pixel and convert the assessment into a corresponding color (e.g., a color range from red for bad health to blue for good health for a range of numerical scores, a binary color scheme of red for bad health and blue for good health for binary outcomes, and the like). The pixels of each facial region may be set to an appropriate color, value, shade, and the like, based on the assessment of skin health at the location of the pixel to generate the visual map. The visual map may then be displayed to the customer 110 via the display 114 of the mobile endpoint device 108.

The image processing engine 306 may also define the boundaries for each facial region that was identified for touch interaction, format the assessment of facial skin health 116 to be compatible with a particular mobile endpoint device 108, and the like.

In one embodiment, the chromophore separation engine 308 may perform a constrained independent component analysis on the spectral representation of the image 112 to obtain three independent components. In one embodiment, the three independent components may be a melanin component, a hemoglobin component, and a shading component. In one embodiment, obtaining a separate shading component allows the shading component to be removed from the graphical chromophore maps of the melanin and hemoglobin, thereby providing more accurate graphical chromophore maps.

In one embodiment, the melanin component and the hemoglobin component may be used to determine the melanin content and the hemoglobin content within the facial regions of the image 112. The melanin content and the hemoglobin content may be scored (e.g., binary outcome or numerical value) as be used as parameters for generating the visual map and/or for the assessment of facial skin health 116.

In one embodiment, the independent components may be obtained from the spectral representation of the image 112 using a constrained independent component analysis (ICA). One example of the constrained ICA is described in co-pending U.S. Patent Provisional Application Ser. No. 62/311,175, entitled "METHOD AND APPARATUS FOR GENERATING GRAPHICAL CHROMOPHORE MAPS," filed on Mar. 21, 2016, which is incorporated by reference in its entirety.

In one embodiment, the graphical chromophore map generator 310 may then generate a graphical chromophore map for one or more of the independent components that are separated. In one embodiment, the graphical chromophore map generator 310 may generate a hemoglobin graphical chromophore map and a melanin graphical chromophore map. The graphical chromophore maps may illustrate or display the texture of the facial skin of the customer 110. For example the texture may reveal moles, pores and other skin imperfections.

In one embodiment, the wrinkle detection engine 312 may detect wrinkles in the image 112 and provide highlighting or markings for the wrinkles that are detected. In one embodiment, a Hessian based Frangi Filtering operation may be applied to the facial regions that are identified from the image 112 to detect the wrinkles. A morphological filtering operation may be applied to remove spurious edges that are detected as potential wrinkles by the Hessian based Frangi Filtering operation. The remaining edges may be analyzed further using a connected component analysis, and an ellipse can be fit around each connected component. A length of a major and minor axis of the ellipse, and as well as an area and an orientation (e.g., vertically aligned wrinkles and horizontally aligned wrinkles) may be stored.

In one embodiment, the wrinkles may be used as one parameter for calculating and displaying the assessment of facial skin health 116. In one embodiment, threshold values associated with a number of wrinkles may be used for scoring. For example, based on an age and gender of the customer 110 a threshold of an overall number of wrinkles or a number of wrinkles per facial region may be predefined (e.g., 20 for an overall facial skin image, 10 in an eye region, 0 in a chin region, 5 in a cheek region, and the like). If the number of wrinkles is above the threshold, the assessment may be bad or if the number of wrinkles is below the threshold, the assessment may be good for binary outcomes. Alternatively, the number of wrinkles may be correlated to a numerical score (e.g., 0-2 wrinkles may be 100, 3-4 wrinkles may be 90, 5-6 may be 80, and so forth, for example).

In one embodiment, the pore detection engine 314 may detect pores in the image 112 and provide circular outlines of the pores that are detected. In one embodiment, any operation for detecting pores may be used. In one embodiment, the pores may be detected based on a circular Hough transform.

In one embodiment, the pores or the skin texture may be used as one parameter for calculating and displaying the assessment of facial skin health 116. In one embodiment, threshold values associated with a number of pores may be used for scoring. In another example, a histogram plot or Canfield scores for skin texture severity scores may be used for scoring.

In one embodiment, the metadata generation engine 316 may annotate the assessment of facial skin health 116 with metadata 118. The metadata 118 may include a date and time that the image 112 was taken, a date and time the assessment of facial skin health 116 was generated, answers to questions that were received via the contextual input from the customer 110, details of the one or more parameters that are analyzed for each one of the different facial regions that will be displayed in the assessment of facial skin health 116, and the like.

Referring back to FIG. 1, the FSAS 104 may generate the assessment of facial skin health 116 based on analysis and processing of the image 112 taken by the mobile endpoint device 108 of the customer 110. The FSAS 104 may then transmit the assessment of facial skin health 116 and the metadata 118 that is generated back to the mobile endpoint device 108. The assessment of facial skin health 116 may then be displayed to the customer 110 via the display 114 of the mobile endpoint device 108 as illustrated by example in FIG. 5.

Thus, the present disclosure provides a system and method that analyzes a mobile selfie image, determines an assessment of facial skin health based on the mobile selfie image and transmits the assessment of facial skin health back to the customer. Selfie images may be occasionally taken of the customer 110 and transmitted to the FSAS 104 for analysis. The mobile endpoint device 108 can track the health status of the facial skin of the customer 110 over time via graphs, charts, reports, and the like. As a result, the customer 110 may determine an overall trend of his or her facial skin and also be provided recommendations for action, skin care products, and the like, based on the facial skin health status trend of the customer 110.

Figure 6:
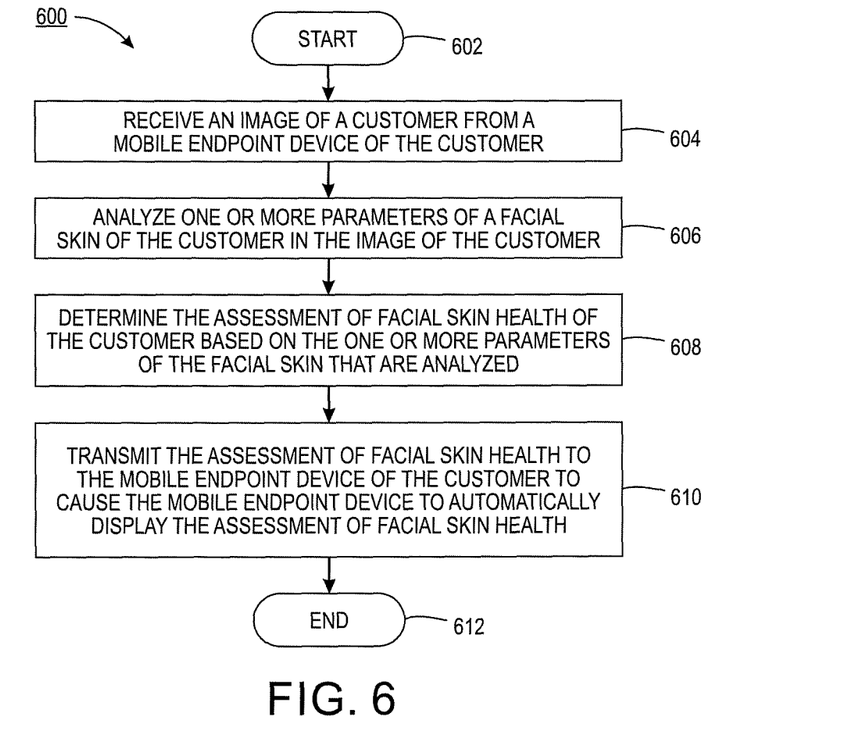
FIG. 6 illustrates a flowchart of an example method for transmitting an assessment of facial skin health of a customer.
Figure 7:
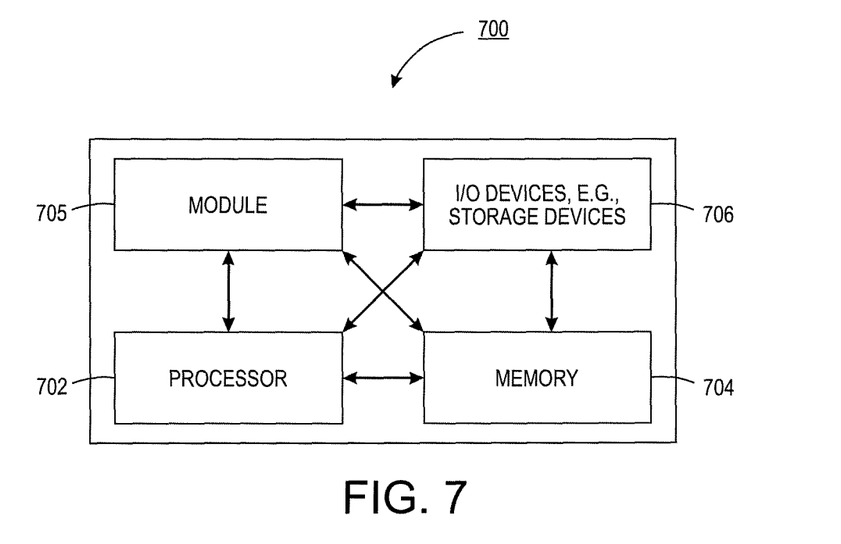
FIG. 7 illustrates a high-level block diagram of a computer suitable for use in performing the functions described herein.

FIG. 6 illustrates a flowchart of an example method 600 for transmitting an assessment of facial skin health of a customer. In one embodiment, one or more steps or operations of the method 600 may be performed by the FSAS 104 or a computer as illustrated in FIG. 7 and discussed below.

At block 602, the method 600 begins. At block 604, the method 600 receives an image of a customer from a mobile endpoint device of the customer. For example, the customer may take a mobile selfie image that includes a face of the customer at a proper orientation, size and lighting. The customer may be guided by the mobile endpoint device to position the customer's face or head properly to capture the image that can be analyzed.

At block 606, the method 600 analyzes one or more parameters of a facial skin of the customer in the image of the customer. In one embodiment, the one or more parameters may include a melanin content of the facial skin, a hemoglobin content of the facial skin, one or more wrinkles of the facial skin and a texture of the facial skin. The texture of the facial skin may be used to identify moles, pores, acne, and other skin imperfections, of the customer. The methods and techniques described above for each one of the one or more parameters may be used to analyze the one or more parameters from the image of the customer.

At block 608, the method 600 determines the assessment of facial skin health of the customer based on the one or more parameters of the facial skin that are analyzed. For example, the analysis of the one or more parameters of the facial skin may be converted into a binary outcome, a score, or a numerical value. In one embodiment, the one or more parameters may be analyzed for each facial region. In one embodiment, the one or more parameters may be analyzed for each pixel of each facial region.

In one embodiment, the binary outcome may be determined based upon a respective threshold of a parameter. For example, if the binary outcome may be determined based upon the parameter breaching the respective threshold (e.g., the binary outcome may be good for being above the threshold and bad for being below the threshold for some parameters and bad for other parameters).

In one embodiment, the score or numerical value may be based on the one or more parameters that are analyzed. For example, a conversion may be used to convert the analysis of the parameter to the numerical value or score. For example, having 0-5 wrinkles may be converted to a score of 100, having 6-10 wrinkles may be converted to a score of 90 and so forth. In another example, having a melanin content in the facial skin that is in the 90th percentile and above may be converted to a score of 100, having a melanin content that is in the 80th percentile may be converted to a score of 90, and so forth.

In one embodiment, the binary outcome or the numerical value may be converted into a visual map. For example, each facial region may have color coded areas based on the binary outcome or numerical value of the one or more parameters. For example, the visual map may have gradually changing colors similar to a heat map or have binary colors for binary outcomes. In one embodiment, each parameter may have a respective visual map. For example, a visual map may be created for an overall assessment of facial skin health, a visual map may be created for a melanin content, a visual map may be created for a hemoglobin content, a visual map may be created for wrinkles, a visual map may be created for texture, and the like.

In one embodiment, the numerical values may be weighted to calculate the assessment of facial skin health. For example, some parameters may be defined to be more important than other parameters and be weighted accordingly. In another embodiment, the customer may provide input regarding a particular parameter that is important to him or her. As a result, the particular parameter may be weighted more heavily than the other parameters for the assessment of facial skin health.

At block 610, the method 600 transmits the assessment of facial skin health to the mobile endpoint device of the customer to cause the mobile endpoint device to automatically display the assessment of facial skin health. For example, the assessment of facial skin health may be displayed as a binary outcome (e.g., good or bad). In another example, the assessment of facial skin health may be displayed as a numerical score (e.g., 1-100). In another example, the assessment of facial skin health may be displayed as a visual map. The customer may review his or her assessment of facial skin health and take action accordingly. At block 612, the method 600 ends.

It should be noted that although not explicitly specified, one or more steps, functions, or operations of the method 600 described above may include a storing, displaying and/or outputting step as required for a particular application. In other words, any data, records, fields, and/or intermediate results discussed in the methods can be stored, displayed, and/or outputted to another device as required for a particular application.

FIG. 7 depicts a high-level block diagram of a computer that can be transformed into a machine that is dedicated to perform the functions described herein. As a result, the embodiments of the present disclosure improve the operation and functioning of the computer (e.g., the FSAS 104) to improve methods for transmitting an assessment of facial skin health of a customer, as disclosed herein.

As depicted in FIG. 7, the computer 700 comprises one or more hardware processor elements 702 (e.g., a central processing unit (CPU), a microprocessor, or a multi-core processor), a memory 704, e.g., random access memory (RAM) and/or read only memory (ROM), a module 705 for transmitting an assessment of facial skin health of a customer, and various input/output devices 706 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the computer may employ a plurality of processor elements. Furthermore, although only one computer is shown in the figure, if the method(s) as discussed above is implemented in a distributed or parallel manner for a particular illustrative example, i.e., the steps of the above method(s) or the entire method(s) are implemented across multiple or parallel computers, then the computer of this figure is intended to represent each of those multiple computers. Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented.

It should be noted that the present disclosure can be implemented in software and/or in a combination of software and hardware, e.g., using application specific integrated circuits (ASIC), a programmable logic array (PLA), including a field-programmable gate array (FPGA), or a state machine deployed on a hardware device, a computer or any other hardware equivalents, e.g., computer readable instructions pertaining to the method(s) discussed above can be used to configure a hardware processor to perform the steps, functions and/or operations of the above disclosed methods. In one embodiment, instructions and data for the present module or process 705 for transmitting an assessment of facial skin health of a customer (e.g., a software program comprising computer-executable instructions) can be loaded into memory 704 and executed by hardware processor element 702 to implement the steps, functions or operations as discussed above in connection with the exemplary method 600. Furthermore, when a hardware processor executes instructions to perform "operations," this could include the hardware processor performing the operations directly and/or facilitating, directing, or cooperating with another hardware device or component (e.g., a co-processor and the like) to perform the operations.

The processor executing the computer readable or software instructions relating to the above described method(s) can be perceived as a programmed processor or a specialized processor. As such, the present module 705 for transmitting an assessment of facial skin health of a customer (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. More specifically, the computer-readable storage device may comprise any physical devices that provide the ability to store information such as data and/or instructions to be accessed by a processor or a computing device such as a computer or an application server.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method for transmitting an assessment of facial skin health of a customer, comprising:
   receiving, by a processor, an image of the customer from a mobile endpoint device of the customer;
   analyzing, by the processor, one or more parameters of a facial skin of the customer in each pixel of the image of the customer;
   determining, by the processor, the assessment of facial skin health of the each pixel of the image of the customer based on the one or more parameters of the facial skin that are analyzed;
   associating, by the processor, a corresponding color to the each pixel based on the assessment of facial skin health that is determined for the each pixel;
   generating, by the processor, a visual map based on the corresponding color that is associated with the each pixel based on the assessment of facial skin health that is determined for the each pixel, wherein the visual map comprises a plurality of facial regions that include concentric areas having a different color based on the corresponding color that is associated with the each pixel; and
   transmitting, by the processor, the assessment of facial skin health that includes the visual map to the mobile endpoint device of the customer to cause the mobile endpoint device to automatically display the assessment of facial skin health.

2. The method of claim 1, wherein the analyzing the one or more parameters is performed for each one of a plurality of different facial regions.

3. The method of claim 1, wherein the one or more parameters comprise a melanin content of the facial skin, a hemoglobin content of the facial skin, one or more wrinkles of the facial skin, one or more pores of the facial skin and a texture of the facial skin.

4. The method of claim 3, wherein the melanin content of the facial skin and the hemoglobin content of the facial skin are analyzed based upon a modified independent component analysis performed on the image to obtain a melanin component and a hemoglobin component from the image.

5. The method of claim 3, wherein the one or more wrinkles are identified by applying a Hessian based Frangi Filtering operation on the image.

6. The method of claim 3, wherein the texture of the facial skin is obtained based on a local binary patterns analysis and a random forest regression analysis applied to the image.

7. The method of claim 1, wherein the assessment of facial skin health comprises a binary outcome based upon each one of the one or more parameters being above a respective threshold value.

8. The method of claim 1, wherein the assessment of facial skin health comprises a numerical score based upon a weighted score of each one of the one or more parameters.

9. A non-transitory computer-readable medium storing a plurality of instructions, which when executed by a processor, cause the processor to perform operations for transmitting an assessment of facial skin health of a customer, the operations comprising:
receiving an image of the customer from a mobile endpoint device of the customer;
analyzing one or more parameters of a facial skin of the customer in each pixel of the image of the customer;
determining the assessment of facial skin health of the each pixel of the image of the customer based on the one or more parameters of the facial skin that are analyzed;
associating a corresponding color to the each pixel based on the assessment of facial skin health that is determined for the each pixel;
generating a visual map based on the corresponding color that is associated with the each pixel based on the assessment of facial skin health that is determined for the each pixel, wherein the visual map comprises a plurality of facial regions that include concentric areas having a different color based on the corresponding color that is associated with the each pixel; and
transmitting the assessment of facial skin health that includes the visual map to the mobile endpoint device of the customer to cause the mobile endpoint device to automatically display the assessment of facial skin health.

10. The non-transitory computer-readable medium of claim 9, wherein the analyzing the one or more parameters is performed for each one of a plurality of different facial regions.

11. The non-transitory computer-readable medium of claim 9, wherein the one or more parameters comprise a melanin content of the facial skin, a hemoglobin content of the facial skin, one or more wrinkles of the facial skin, one or more pores of the facial skin and a texture of the facial skin.

12. The non-transitory computer-readable medium of claim 11, wherein the melanin content of the facial skin and the hemoglobin content of the facial skin are analyzed based upon a modified independent component analysis performed on the image to obtain a melanin component and a hemoglobin component from the image.

13. The non-transitory computer-readable medium of claim 11, wherein the one or more wrinkles are identified by applying a Hessian based Frangi Filtering operation on the image.

14. The non-transitory computer-readable medium of claim 11, wherein the texture of the facial skin is obtained based on a local binary patterns analysis and a random forest regression analysis applied to the image.

15. The non-transitory computer-readable medium of claim 9, wherein the assessment of facial skin health comprises a binary outcome based upon each one of the one or more parameters being above a respective threshold value.

16. The non-transitory computer-readable medium of claim 9, wherein the assessment of facial skin health comprises a numerical score based upon a weighted score of each one of the one or more parameters.

17. A method for transmitting an assessment of facial skin health of a customer, comprising:
receiving, by a processor, an image of the customer from a mobile endpoint device of the customer;
analyzing, by the processor, a melanin content, a hemoglobin content, one or more wrinkles, one or more pores and a texture for each one of a plurality of different facial regions of a facial skin of the customer in each pixel of the image of the customer;
calculating, by the processor, a respective score for the melanin content, the hemoglobin content, the one or more wrinkles, the one or more pores and the texture based on the analyzing;
determining, by the processor, the assessment of facial skin health of the each pixel of the image of the customer based on the respective score that is calculated for the melanin content, the hemoglobin content, the one or more wrinkles, the one or more pores and the texture of the facial skin;
associating, by the processor, a corresponding color to the each pixel based on the assessment of facial skin health that is determined for the each pixel;
generating, by the processor, a visual map based on the corresponding color that is associated with the each pixel based on the assessment of facial skin health that is determined for the each pixel, wherein the visual map comprises a plurality of facial regions that include concentric areas having a different color based on the corresponding color that is associated with the each pixel; and
transmitting, by the processor, the assessment of facial skin health that includes the visual map to the mobile endpoint device of the customer to cause the mobile endpoint device to automatically display the assessment of facial skin health.

* * * * *